(12) United States Patent
Guentert et al.

(10) Patent No.: US 10,149,734 B2
(45) Date of Patent: Dec. 11, 2018

(54) PIVOTABLE OPTICAL ASSEMBLY FOR A SURGICAL MICROSCOPE, IN PARTICULAR 0°-ASSISTANT'S DEVICE, AND A RETAINING SYSTEM FOR SAID PIVOTABLE OPTICAL ASSEMBLY OF THE SURGICAL MICROSCOPE

(71) Applicant: Leica Instruments (Singapore) Pte. Ltd., Singapore (SG)

(72) Inventors: Michael Guentert, Heerbrugg (CH); Curdin Schlumpf, Winterthur (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 63 days.

(21) Appl. No.: 15/206,432

(22) Filed: Jul. 11, 2016

(65) Prior Publication Data

US 2017/0020624 A1    Jan. 26, 2017

(30) Foreign Application Priority Data

Jul. 24, 2015    (EP) .................................... 15178177

(51) Int. Cl.
*A61B 90/20*    (2016.01)
*A61B 90/25*    (2016.01)
(Continued)

(52) U.S. Cl.
CPC .............. *A61B 90/25* (2016.02); *A61B 90/20* (2016.02); *G02B 21/0012* (2013.01); *G02B 21/18* (2013.01); *G02B 21/24* (2013.01)

(58) Field of Classification Search
CPC .. B23Q 1/0063; G02B 21/0012; G02B 21/18; G02B 21/24; E05C 1/14; E05C 1/163;
(Continued)

(56) References Cited

U.S. PATENT DOCUMENTS 1,131,542 A    3/1915 Olsen
3,628,386 A *  12/1971 Blum .................... G01B 3/004
                                                    74/89.14
(Continued)

FOREIGN PATENT DOCUMENTS

JP    S5141816 B1    11/1976
JP    2013064246 A    4/2013

*Primary Examiner* — Cara E Rakowski
(74) *Attorney, Agent, or Firm* — Hodgson Russ LLP

(57) ABSTRACT

The present invention provides a pivotable optical assembly for a surgical microscope, specifically a zero-degree assistant's device, the assembly comprising: a microscope body interface for mounting the assembly on a microscope body; an assistant's module including an interface for an assistant's tube, the assistant's module being pivotable about a pivot axis relative to the microscope body; and a retaining system that blocks pivoting the assistant's module about the pivot axis. The retaining system comprises: a retaining element being moveable from a locking position into a release position, a biasing member forcing the retaining element into the locking position, and a hand-operable control element acting on the retaining element for moving it from the locking position into the release position, as well as a pivotable optical assembly comprising said retaining system according to the invention, whose retaining element, in its blocking position, blocks pivoting the assistant's module about the pivot axis.

6 Claims, 8 Drawing Sheets

Figure 1:
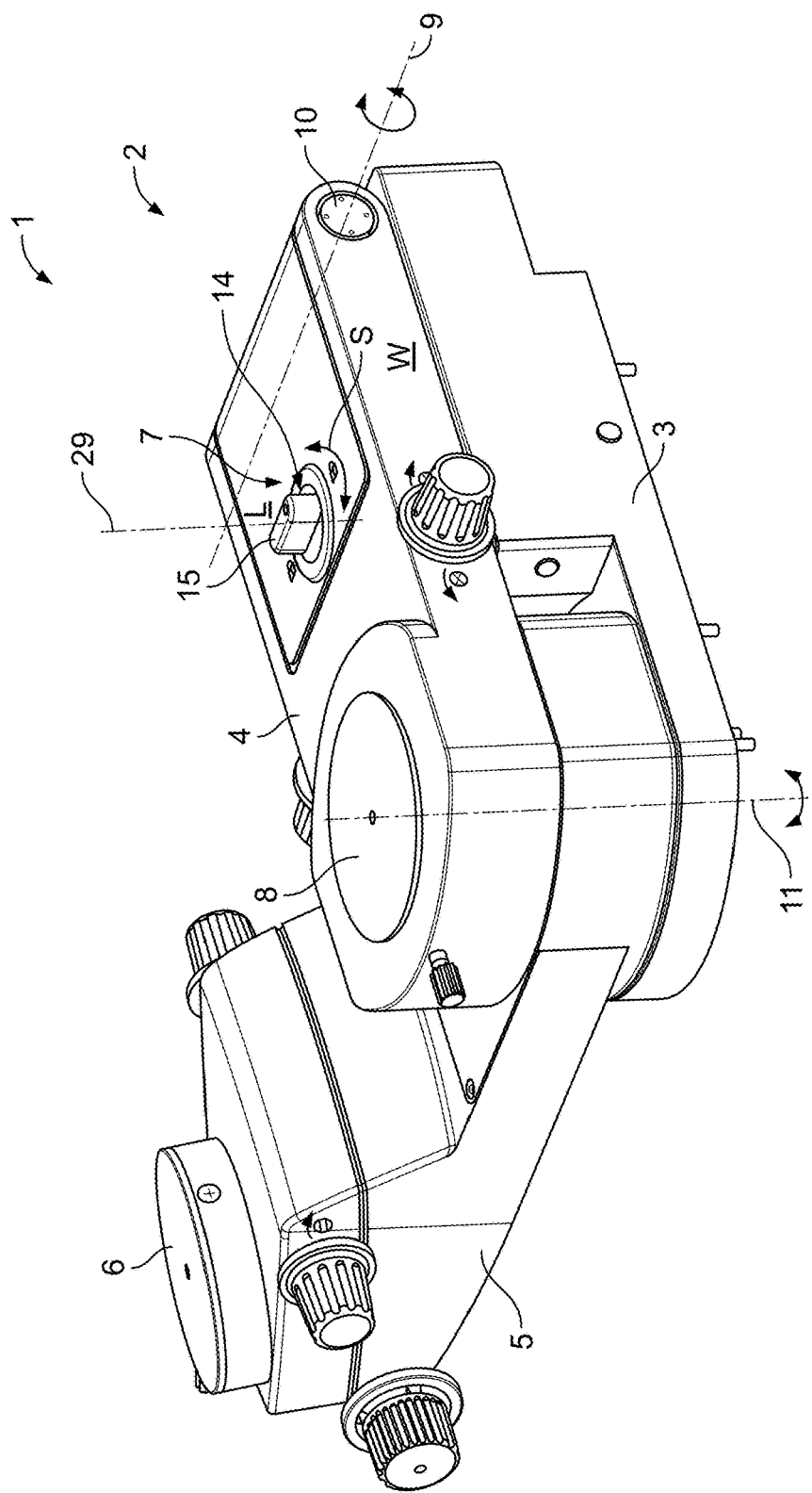

(51) Int. Cl.
  *G02B 21/00*   (2006.01)
  *G02B 21/18*   (2006.01)
  *G02B 21/24*   (2006.01)

(58) Field of Classification Search
  CPC . E05C 1/16; A61B 90/25; A61B 90/20; E05B
        13/002; E05B 13/005; E05B 13/10; E05B
                              13/101; E05B 13/105
  USPC ................ 292/169, 175, 163, 164, 137, 138
  See application file for complete search history.

(56) References Cited

U.S. PATENT DOCUMENTS

| | | | |
|---|---|---|---|
| 3,933,380 A | * | 1/1976 | Wellekens ............... E05B 55/12 |
| | | | 292/169.13 |
| 4,344,595 A | * | 8/1982 | Heller .................... A61B 90/25 |
| | | | 248/542 |
| 6,421,173 B1 | | 7/2002 | Corbisiero et al. |
| 2006/0215258 A1 | | 9/2006 | Strobel et al. |

* cited by examiner

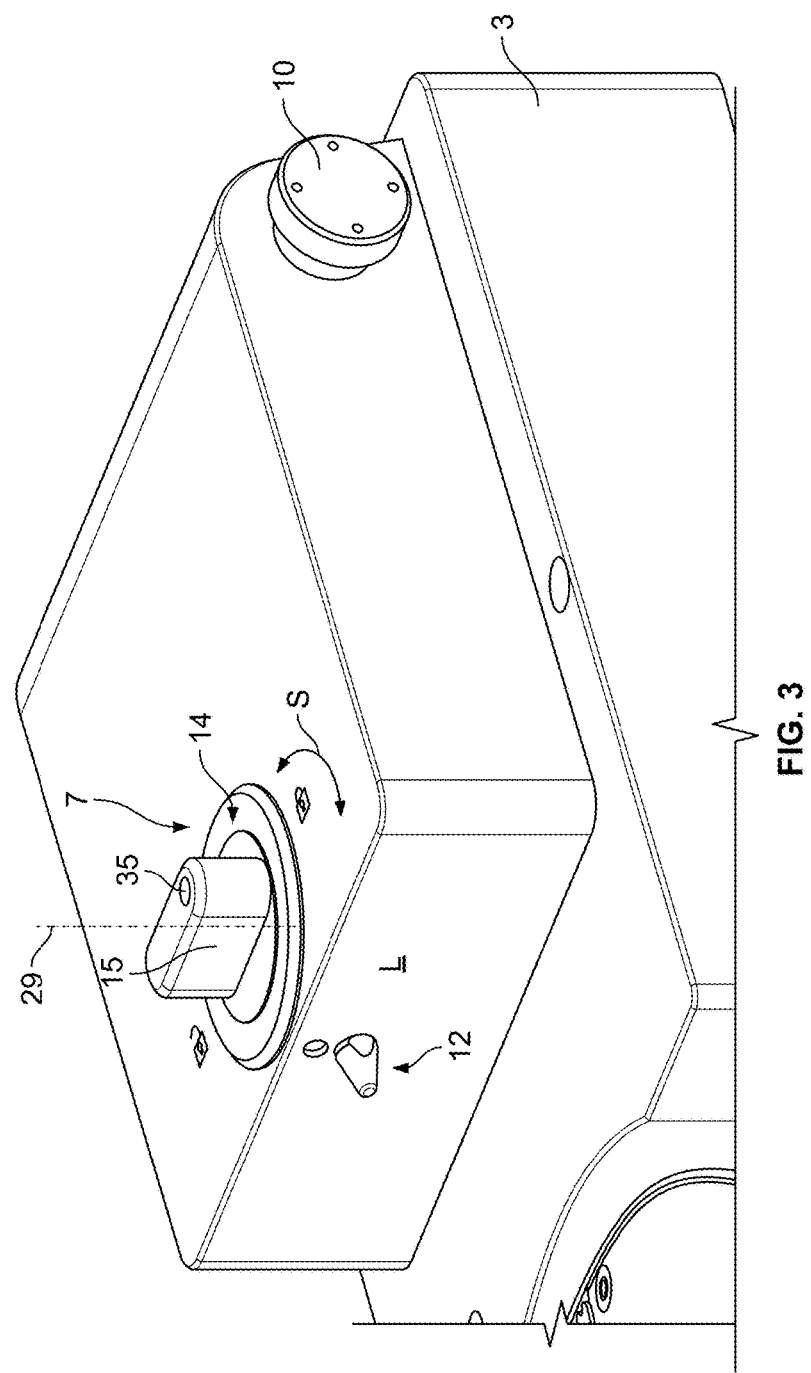

PIVOTABLE OPTICAL ASSEMBLY FOR A SURGICAL MICROSCOPE, IN PARTICULAR 0°-ASSISTANT'S DEVICE, AND A RETAINING SYSTEM FOR SAID PIVOTABLE OPTICAL ASSEMBLY OF THE SURGICAL MICROSCOPE

The present invention concerns a pivotable optical assembly for a surgical microscope, in particular a 0°-assistant's device. The assembly comprises a microscope body interface for mounting the assembly on a microscope body; an assistant's module including an interface for an assistant's tube, the assistant's module being pivotable about a pivot axis relative to the microscope body interface; and a retaining system for blocking pivoting the assistant's module about the pivot axis. The present invention further concerns a retaining system for such pivotable optical assembly of a surgical microscope.

In such pivotable optical assemblies, the optical beam path can be coupled out of the beam path for a principle observer and be deflected into an assistant's device so that the acquired microscope image can be made accessible not only to the principle observer but also to a further observer (hereafter called an "assistant"). Such systems are often used in surgical microscopes, in particular for ophthalmology. They allow the operation to be followed not only by the principle observer or lead surgeon, but also by an assistant. Commonly, the pivotable optical assembly, in particular a 0°-assistant device deflects the beam path (or portion thereof) into the corresponding assistant's tube, the beam path in the assistant's tube and in the principle observer's tube being at a 90° to one another. In common pivotable optical assemblies, a 0°-assistant insert is used that deflects the beam path into the assistant's tube. Such 0°-assistants inserts are connected, via a suitable connecting mechanism, to the microscope body on the one side and to the binocular tube for the principle observer on the other.

In-between surgeries or examinations, it is often necessary to change the position of the assistant. With a 0°-assistant's insert, this can be done only by disassembling the insert, rotating it about 180° (from left to right or right to left), and realigning and reinstalling the insert.

In the context of surgical microscopes, it is extremely impractical, complex and dangerous to disassemble, reorient and restore the 0°-assistant's insert, as well as the principle observer's tube, and other components of the surgical microscope that may be present, whenever the assistant changes sides, especially if the assistant needs to change sides during an operation. Further, the risk exists that the part being disassembled and installed may collide or be damaged when changing the orientation. Stereo microscopes having an assistant's insert and a separate illumination module, the illumination module and the assistant's insert being able to assume at least two different positions by rotation about an axis are generally known in the art. The construction of such known microscopes is such that the distance between the assistant's tube and the principle observer's tube must in any case always be sufficient to ensure collision-free rotation of the assistant's tube. The result of this, however, is that the microscopes overall height is undesirably high.

DE 10 2005 040 580 A1 discloses a 0°-assistant's device comprising a pivotable assistant's module. In order to be able to pivot the module, a captive screw needs to be unscrewed from the microscope body interface, which is time consuming and requires equipment for disengaging the screws.

It is therefore the object of the present invention to provide a pivotable optical assembly for a surgical microscope and a retaining system therefor, that allows the assistant to change sides quickly, easily and without the requirement of separate equipment.

This object is achieved by a retaining system for a pivotable optical assembly of a surgical microscope, the retaining system comprising a retaining element being moveable from a locking position into a release position, a biasing member forcing the retaining element into the locking position, and a hand-operable control element acting on the retaining element for moving it from the locking position into the release position. For the pivotable optical assembly initially mentioned, this object is achieved in that the assembly comprises a retaining system of the present invention, whose retaining element, in its locking position, blocks pivoting the assistant's module about the pivot axis.

The hand-operable control element that is capable of moving the retaining element into the release position renders the use of separate equipment moot. Further, it makes an unrestricted pivoting of the assistant's module possible. In its blocking position, the retaining element blocks pivoting of the assistant's module, whereas, after moving the retaining element from the locking position into the release position by operating the hand-operable control element, pivoting of the assistant's module is possible.

It should be noted that the present invention is also applicable without restriction to optical assemblies in which, instead of an interface for an optical connection, a fixed connection to that optical component is provided. The expression "interface for an assistant's tube" is consequently also to be understood to signify that the relevant assistant's tube is connected to or embodied with the assistant's module in fixed or integral fashion. The same applies to the tube carrier for the principle observer's tube, so that the tube carrier and the principle observer's tube can also be connected fixedly to one another or embodied integrally.

The essence of the pivotable optical assembly according to the present invention is consequently that the assistant can change sides without the disassembly of accessories or use of separate equipment while the surgical microscope is in use. After the retaining element of the retaining system is brought into the release position by operating the hand-operable control element, pivoting the assistant's module from left to right (e.g. from 0° to 180°) or from right to left (e.g. from 180° to 0°) becomes possible, without the risk of collision with the principle observer's tube, disassembly and re-aligning of the microscope elements connected thereto, use of separate equipment, such as a screwdriver, or risk of losing parts like the unscrewed captive screws.

The inventive solution may be further improved and developed with the following advantageous developments and embodiments, which are independent of each other and can be combined as desired.

According to an embodiment, the pivotable optical assembly may further comprise a tube carrier for a principle observer's tube, the tube carrier being mounted on the microscope body interface. The tube carrier of the pivotable optical assembly may be mounted on the microscope body interface for rotation about a tilt axis relative to the microscope body interface between a working position and an adjustment position, and wherein the assistant's module is pivotable only when the tube carrier is tilted about the tilt axis to the adjustment position. This embodiment avoids accidental pivoting of the assistant's module, when the retaining system is unintentionally in a state where the retaining element is in the release position, as tilting the tube carrier is further necessary, in order to be able to pivot the assistant's module about the pivot axis. This way, a double safety mechanism is achieved, which requires actuation of the retaining system by moving its retaining element into the release position, as well as tilting the tube carrier, before the assistant's module may be pivoted for changing it from left to right or right to left.

In a further embodiment, the retaining element, in its locking position, may block the tube carrier in its working position, this way ensuing that the two actions required to change position of the assistant's modules may only be performed one after the other. First, the retaining element of the retaining system is to be brought into the release position by operating the hand-operable control element. Only after this is done may the tube carrier be tilted about the tilt axis to the adjustment position, which is previously blocked by the retaining element in its locking position. After tilting the tube carrier, the assistant's module may be pivoted.

In one embodiment, the retaining element may engage the tube carrier in its locking position, and, in its release position, is disengaged from the tube carrier in order to ensure that the retaining element blocks the tube carrier in its working position by engagement and allows tilting of the tube carrier in the release position by being disengaged from the tube carrier.

According to a further embodiment, the retaining system may be arranged on the microscope body interface allowing a compact design of the pivotable optical assembly. In one embodiment, the retaining element, in its locking position, protrudes from the microscope body interface and, in its release position, countersinks within the microscope body interface.

In a further embodiment, the microscope body interface may comprise guidance leading the movement of the retaining element between the locking position and the release position. The guidance may avoid problems. It may ensure the correct movement of the retaining element from the locking position into the release position when actuating the retaining system of the present invention, and thus avoids troubles of actuating the hand-operable control element.

In an embodiment of the retaining system, the retaining element may be a locking bolt that is moveable linearly between the locking position into the release position. Such linear direction of movement (which may be a rectilinear or straight-line movement) simplifies the mounting and bearing of the retaining element.

In order to facilitate blocking pivoting the assistant's module, the locking bolt may comprise a beveled locking tip. Such beveled locking tip may be easily brought into engagement with a corresponding locking recess on the assistant's module and/or the tube carrier. Opposite to the beveled locking tip, the locking bolt may comprise a biasing end, which engages with the biasing member that exerts a biasing force to the locking bolt forcing the retaining element into the locking position. This way, it is ensured that the retaining element of the retaining system is in the locking position unless it is intentionally moved into the release position by actuating the hand-operable control element. The locking tip may protrude from the microscope body interface in the locking position, and may countersink within the microscope body interface in the release position, which allows a compact design of the pivotable optical assembly.

In a further embodiment, the locking bolt may comprise a cam that engages with the control element, facilitating the interaction with the control element and allowing a compact design. The cam may not only facilitate moving the retaining element into the release position, but also leading the movement of the retaining element between the locking position and the release position. The guidance can comprise a guide channel accommodating the cam. The guide channel may run along the direction of movement along which the retaining element is moved from its locking position into the release position. Accommodating the cam in the guide channel thus allows leading the movement of the retaining element. Alternatively or additionally, the locking bolt may be accommodated in a guide chamber, the form of which leads its movement.

In one embodiment, the cam may protrude laterally from the locking bolt, allowing a compact and flexible design of the retaining system. The locking bolt can comprise a transverse hole for receiving a fastening section of the cam, allowing an easy provision of a laterally protruding cam, and making it possible to repair the retaining system in case the laterally protruding cam should break.

The fastening section can comprise a thread that is screwed into the transverse hole, allowing to easily providing the locking bolt with a laterally protruding cam. For example, a laterally protruding cam pin having a thread may be provided by screwing a cam pin into the transverse hole, in a manner that the head of the screw laterally protrudes from the hole as a cam pin from the locking bolt.

In a further embodiment, the control element may comprise a pusher that engages with the retaining element. The pusher may be pivotable or rotatable and the control element may act on the retaining element by moving it, e.g. its pusher, from a closed position into an open position. In a compact design, the pusher can comprise an eccentric being mounted rotatable. The eccentric, for example an eccentric disc having a rotating axis which is offset from the centre of the disc, may be mounted rotatable for example on the microscope body interface. In the closed position of the control element, the pusher, such as the eccentric, may be spaced apart from the retaining element, for example, the cam thereof. For actuating the hand-operable control element and transferring it from the closed position to the open position, the pusher may be pivoted/rotated, thereby bringing it into contact and engaging it with the retaining element for moving the retaining element from the locking position into the release position. In an embodiment, where the pusher comprises an eccentric, the cam of the locking bolt, in the locking position, may be spaced apart from the switching axis of the control element of the eccentric less than the radius of the eccentric disc.

According to a further embodiment, the retaining system may further comprise a restraint to hold the control element in the closed position, in which the control element releases the retaining element and the biasing member forces the retaining element into the locking position, and/or in the open position, in which the control element moves the retaining element into the release position. Such restraint ensures that the retaining element is not accidentally moved from the locking position into the release position or vice versa. The restraint ensures that a distinct actuation force is required before the control element may be changed from the closed to the open position or from the open to the closed position. The restraint can further help holding the retaining element in its release position, avoiding that the biasing member forces the retaining element back into the locking position.

In one embodiment, the restraint may comprise a recess and a detent. The recess can be arranged on the control member. In an embodiment, where the restraint holds the control element in the closed position and in the open position, the restraint may comprise two recesses and/or two detents, one of which is assigned to one specific position (i.e. the closed position and the open position). For example, the control element may comprise two recesses; one assigned to the open position, the other assigned to the closed position.

The pusher can comprise a notch as the recess, which is easy to manufacture and allows for a compact design as such a notch may be arranged easily on that part of the control element, which acts on the retaining element.

The retaining element may comprise a first detent that engages with the recess in the open position. The cam may be designed as the first detent, which allows for a compact design as the cam can have a double-function, namely to engage with the control element for moving the retaining element from the locking position into the release position and to form a restraint together with a recess on control element, such as for example a notch on the pusher, holding the control element in the open position once the first detent of the retaining element engages with the recess of the control element.

The retaining system may further comprise a second detent that engages with the recess in the closed position, further ensuring that the retaining element of the retaining system is not accidentally moved into the release position by transferring the control element into the open position. In one embodiment, the actuation force required to move the restraint out of the closed position is greater than the biasing force exerted by the biasing member on the retaining element.

A detent pin, preferably designed as a ball point tensioning screw may form the second detent. Such detent pin may be mounted on the microscope body interface, which may e.g. be provided with a threaded through hole, allowing a flexible design and making it possible to arrange the second detent, in a compact manner, at the desired position for engagement with the recess in the closed position.

In a further embodiment, the first detent and the second detent may be arranged spaced apart from each other in relation to a movement direction, along which the retaining element is moved from its locking position into its release position. In case of a control element comprising a pivotable or rotatable pusher, such as an eccentric that is mounted rotatable, the first detent and the second detent may be arranged opposite to each other in relation to the switching axis of the pusher, so rotating the pusher 180° is required for moving the control element from the open into the closed position, and vice versa.

The invention will now be described in an exemplary manner with reference to the drawings. The advantageous developments and embodiments shown exemplarily in the drawings are independent of each other and can be combined as desired.

Figure 2A:
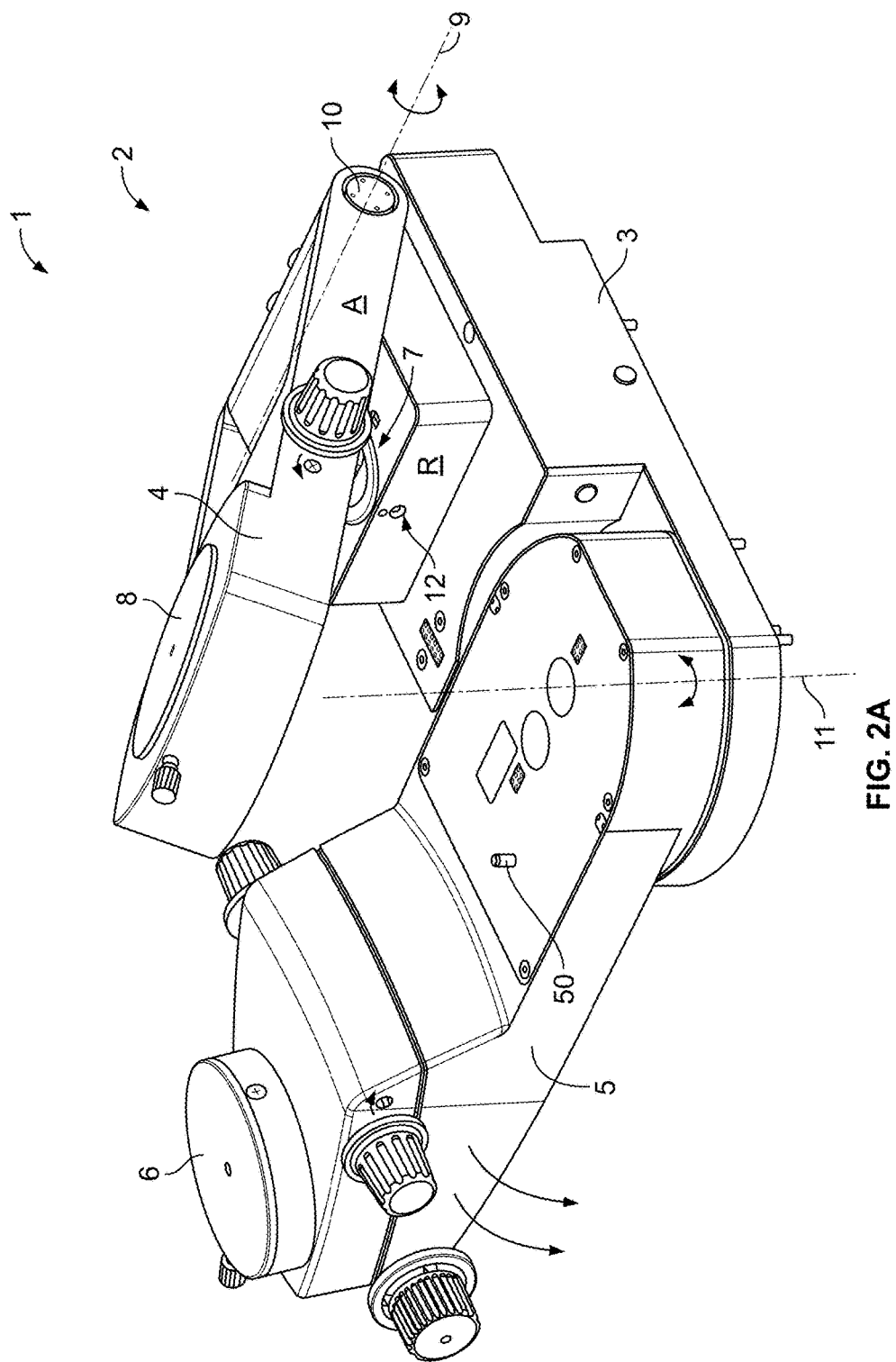
Figure 2B:
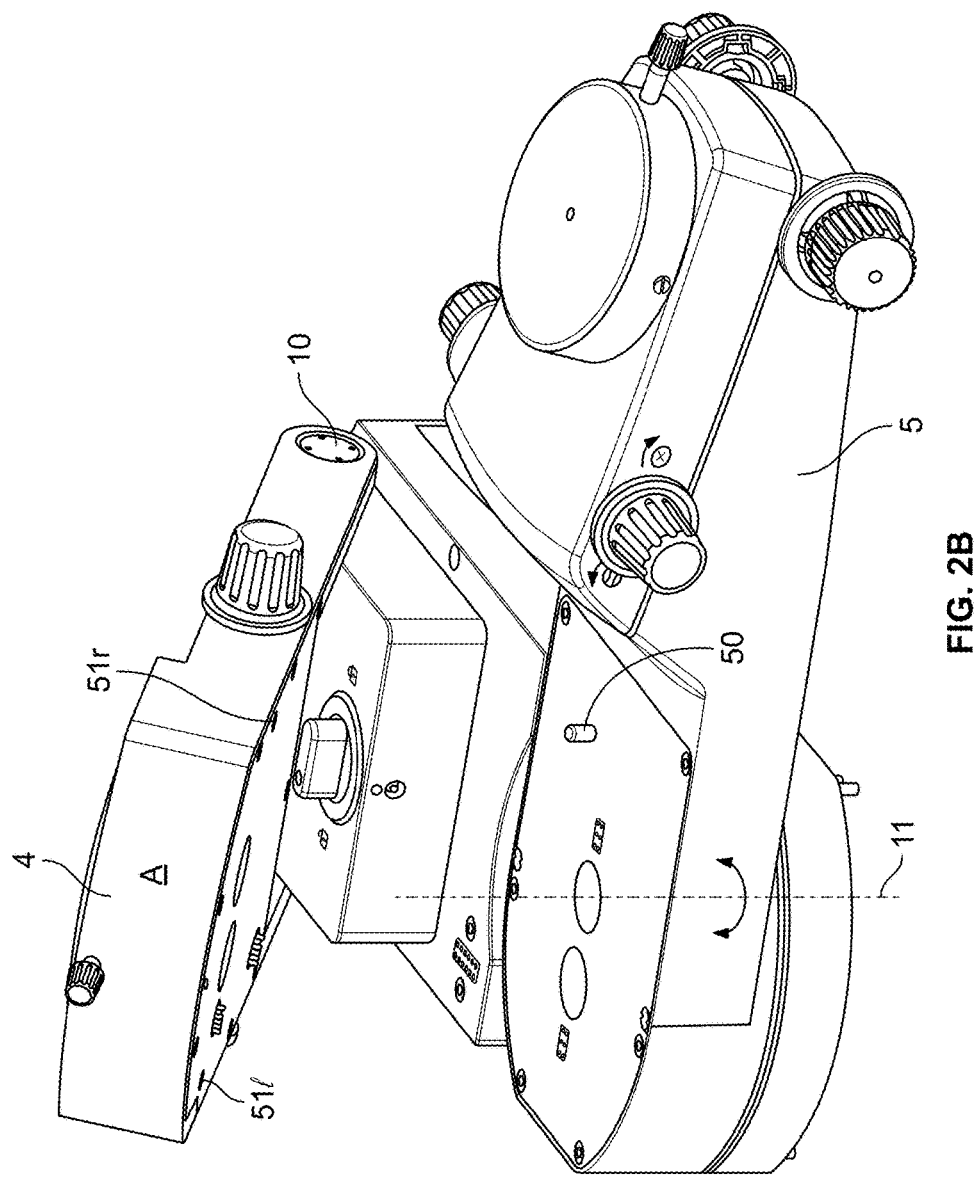
Figure 4:
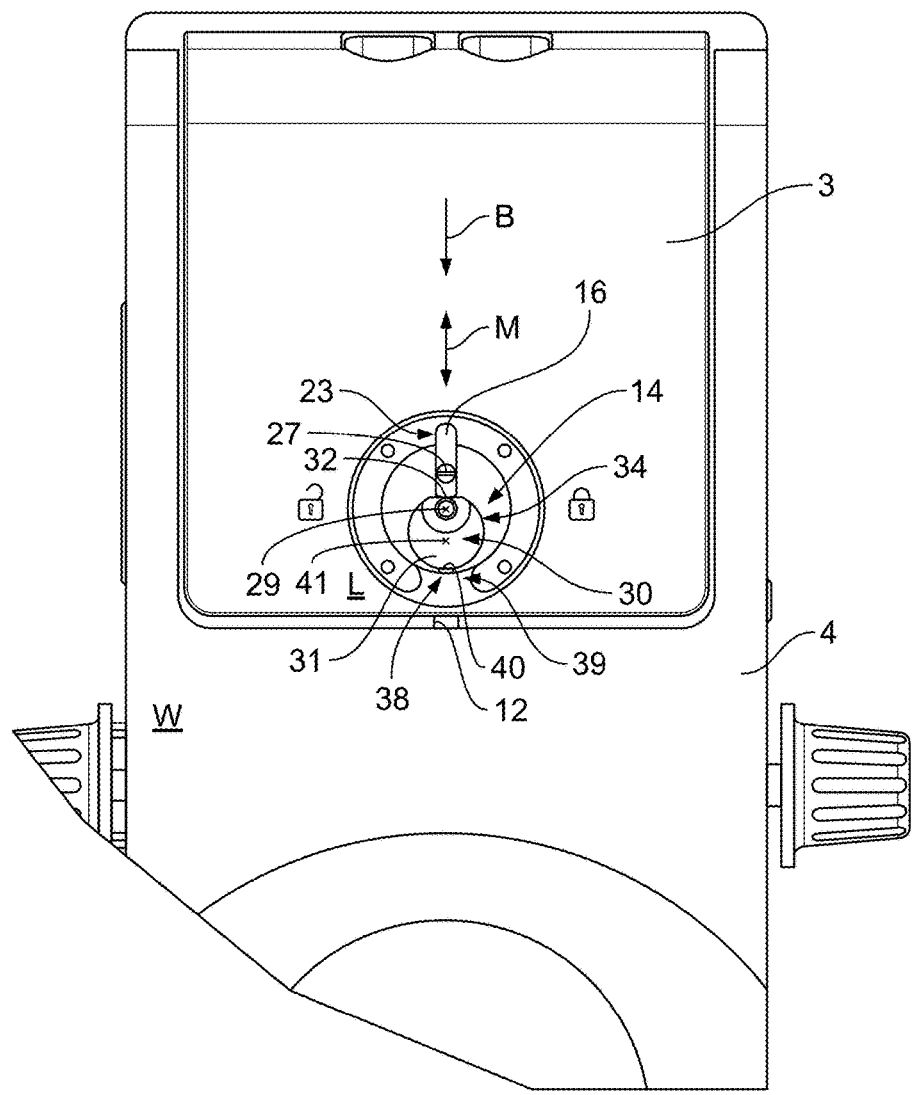
Figure 5:
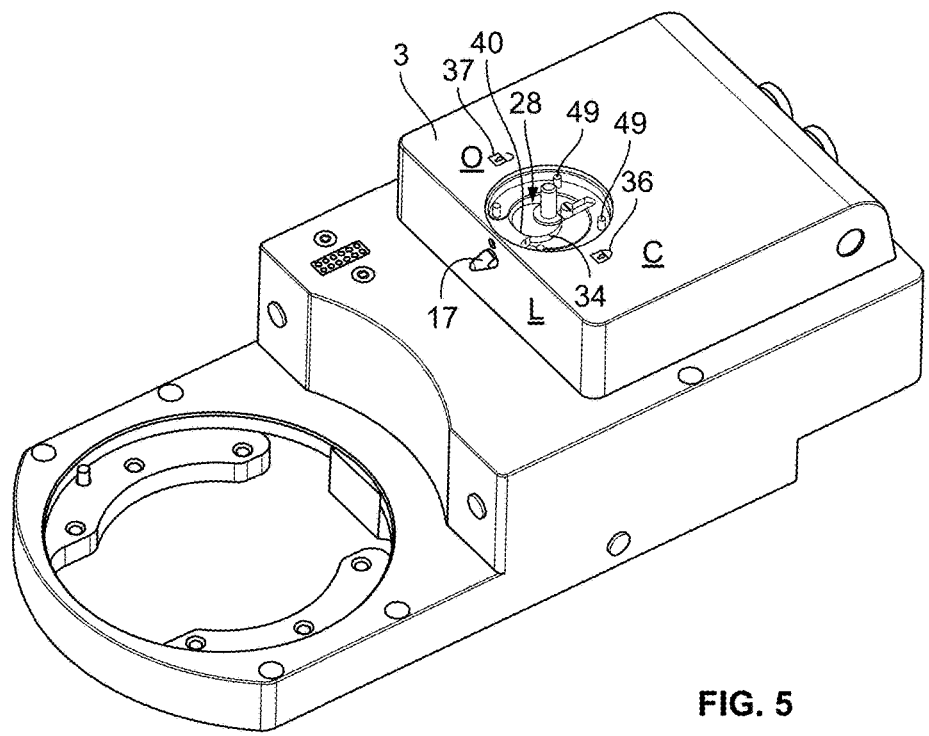
Figure 6:
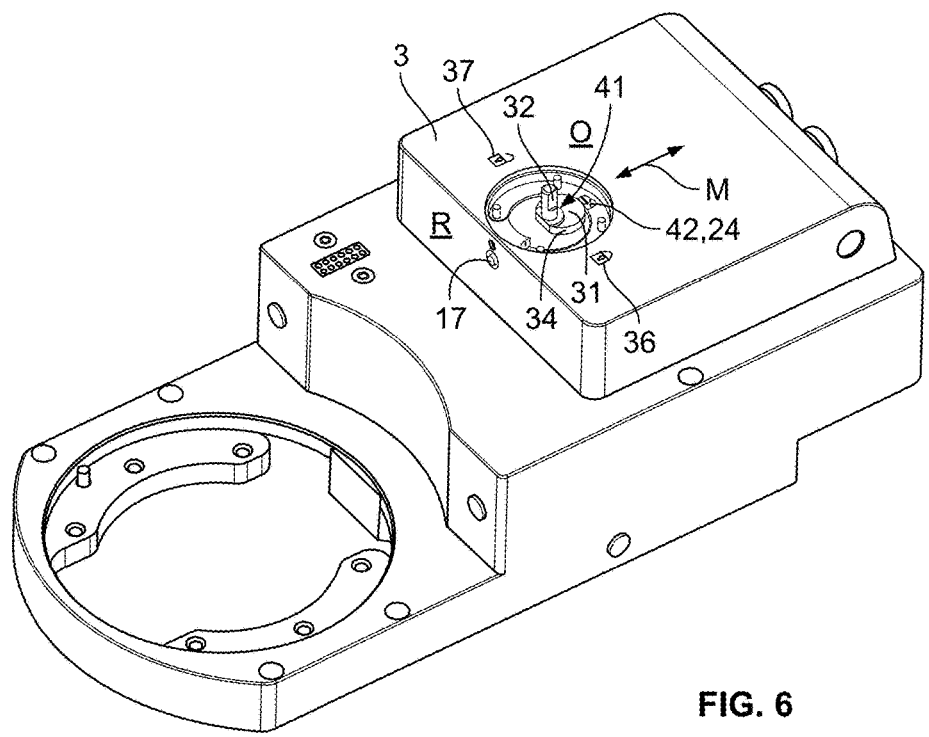
Figure 7:
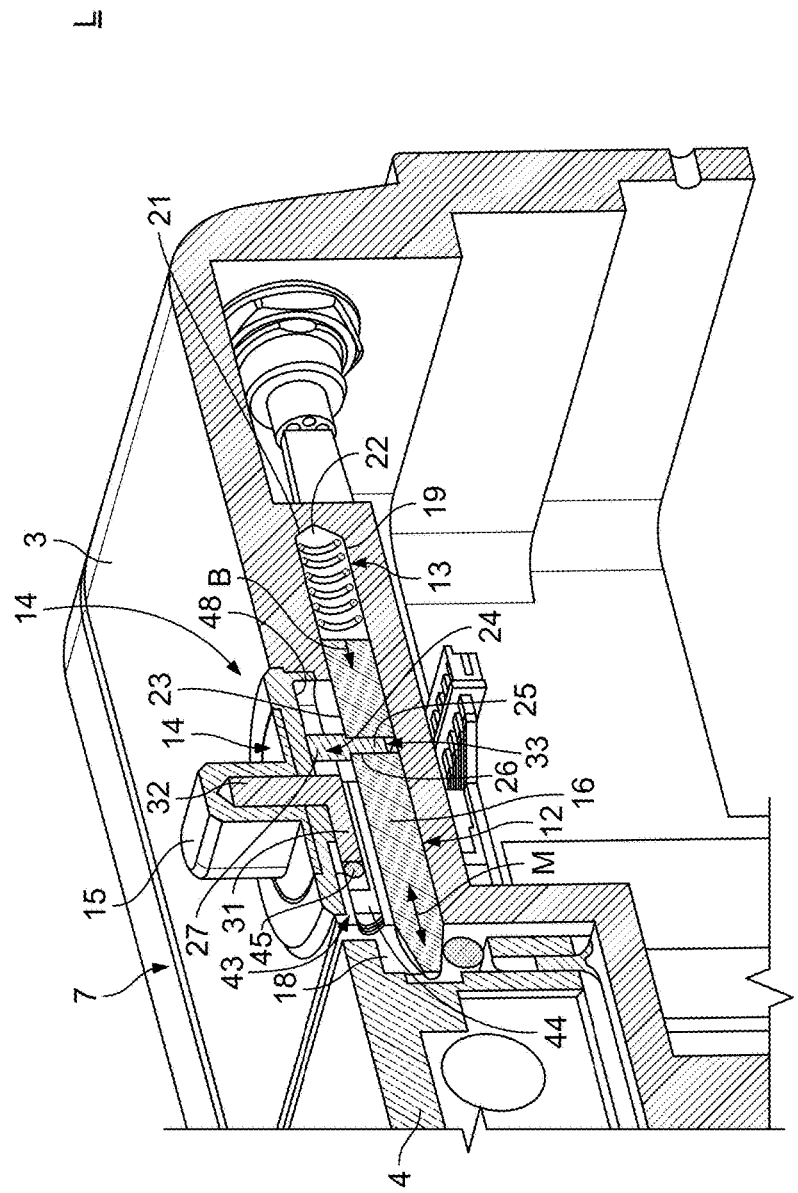
Figure 8:
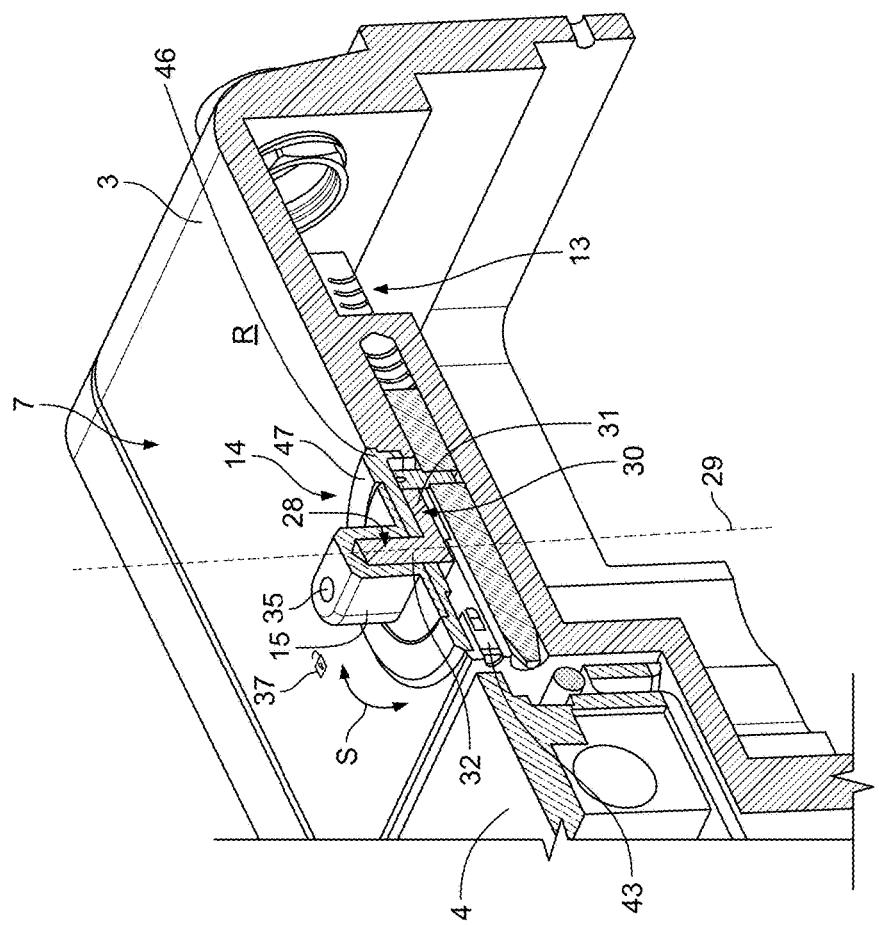

FIG. 1: is a perspective view showing a pivotable optical assembly according to the present invention in a working position;

FIG. 2A: is a perspective view showing the pivotable optical assembly of FIG. 1 in an adjustment position where the tube carrier is tilted and the assistant's module is pivotable;

FIG. 2B: is a perspective view of the assembly shown in FIG. 2A after the assistant's module was pivoted to the other side;

FIG. 3: is a perspective view of a section of the microscope body interface from the pivotable optical assembly of FIG. 1 where the retaining system of the present invention is mounted, shown with the control element in a closed position and the retaining element in the locking position;

FIG. 4: is a top view onto the section of the pivotable optical assembly comprising the retaining system;

FIG. 5: is a perspective view of the microscope body interface of the pivotable optical assembly of FIG. 1, the retaining system thereof being in the locking position;

FIG. 6: is a perspective view of the microscope body interface of the pivotable optical assembly of FIG. 1, the retaining system thereof being in the release position;

FIG. 7: is a sectional view showing an embodiment of the retainer system according to the present invention with the control element in the closed position and the retainer element in the locking position; and FIG. 8: is a sectional view showing an embodiment of the retainer system according to the present invention with the control element in the open position and the retainer element in the release position.

FIG. 1 shows a pivotable optical assembly 1 for a surgical microscope (not shown) according to an exemplary embodiment. In said embodiment, the pivotable optical assembly 1 is a 0°-assistant's device. The assembly 1 shown in FIG. 1 comprises the following components: a microscope body interface 3 for mounting the pivotable optical assembly 1, here the 0°-assistant's device 2 on a microscope body (not shown); a tube carrier 4 for a principle observer's tube (not shown); an assistant's module 5 including an interface 6 for an assistant's tube; and a retaining system 7 according to an exemplary embodiment of the present invention.

The tube carrier 4 comprises an interface 8 for the principle observer's tube. The tube carrier 4 is mounted on the microscope body interface 3 for rotation about a tilt axis 9 relative to the microscope body interface 3 by means of a hinge 10. The tube carrier 4 can be rotated about the tilt axis 9 relative to the microscope body interface 3 between a working position W (shown in FIG. 1) and an adjustment position A (shown in FIGS. 2A and 2B).

The assistant's module 5 is rotatable or pivotable about a pivot axis 11 relative to the microscope body interface 3. If the assistant changes sides, the assistant's module 5 can be pivoted from the position shown in FIG. 1, a 180° to the right (and back again). In order to be able to pivot the assistant's module 5, the retaining system 7 of the present invention, that blocks pivoting of the assistant's module 5 about the pivot axis 11, must be unblocked first. To do so, the retaining element 12 of the retaining system 7 must be moved from a locking position L (shown e.g. in FIGS. 3, 4, 5 and 7) into a release position (shown e.g. in FIGS. 2A, 2B, 6 and 8). A biasing member 13 of the retaining system 7 forces the retaining element 12 into the locking position L, in which the retaining element 2 blocks pivoting of the assistant's module 5 about the pivot axis 11. The retaining element 12 can be moved into the release position R by means of a hand-operable element 14 of the retaining system 7, which acts on the retaining element 12 for moving it from its locking position L into the release position R.

In the shown embodiment, the retaining system 7 of the present invention, in particular the retaining element 12 thereof, indirectly blocks the assistant's module 5. It blocks the tube carrier 4 in the working position W and thus avoids tilting of the tube carrier 4 about the tilt axis 9, which tilting is required to pivot the assistant's module 5. The assistant's module 5, in the shown embodiment, is pivotable only when the tube carrier 4 is tilted above the tilt axis 9 to the adjustment position A. The tube carrier 4 blocks pivoting the assistant's module 5 about the pivot axis 11 in the working position W by a form fit 50, 51l, 51r. The form fit is provided by a spring-biased stud 50 which is arranged on the assistant's module 5 and a corresponding fastening hole 51l, 51r of the tube carrier 4. The spring-biased stud 50 projects in a direction running parallel to the pivot axis 11 from the upper face of the assistant's module 5, which, in the working position W, is adjacent to and aligned with the tube carrier 4. The tube carrier 4 comprises two fastening holes 51*l* and 51*r* in the lower face that is arranged adjacent to the assistant's module 5 in the working position W. The fastening hole 51*l* is aligned with the spring-biased stud 50 when the assistant's module 5 is on the left side (as shown in FIG. 2A). After the tube carrier 4 is brought back into the working position W (which corresponds to the situation in FIG. 1), the spring-biased stud 50 of the assistant's module 5 is accommodated in the fastening hole 51*l*. The interlock between the spring-biased stud 50 and the fastening hole 51*l* avoids pivoting of the assistant's module 5 about the pivot axis 11 in the working position W. If the assistant's module 5 is on the right side, shown in FIG. 2B, pivoting of the assistant's module 5 is blocked similar, except that the spring-biased stud 50 then engages with the fastening hole 51*r*, when the tube carrier 4 is in the working position W.

Thus, as long as the retaining element 12, in its locking position L, blocks the tube carrier 2 in its working position W, the assistant's module 5 may not be pivoted. Of course, alternative embodiments (not shown) are possible, wherein the retaining element 12 directly blocks pivoting of the assistant's module 5.

After the retaining element 12 of the retaining system 1 is moved from its locking position L into the release position R, which will be explained in detail below, the tube carrier 4 may be tilted about the tilt axis 9 from the working position W shown in FIG. 1 to the adjustment position A shown in FIGS. 2A and 2B. The assistant's module 5 may then be pivoted about the pivot axis 11 about 180° from the left (shown in FIG. 1) to the right, as indicated by the arrows in FIG. 2A (and back). After the assistant's module 5 has been pivoted 180° to the right (see FIG. 2B), the tube carrier 4 may be tilted downwards into its working position W (shown in FIG. 1). Then, the retaining system 7 is closed by moving its retaining element 12 back from its release position R, shown in FIGS. 2A and 2B, where it countersinks within the microscope body interface 3, into its locking position L (shown e.g. in FIG. 3, where it protrudes from the microscope body interface 3). This way, the position of the assistant's module 5 may be changed fast and easily without the requirement of specific equipment, and the risk of losing or damaging parts. Further, an unintentional pivoting of the assistant's module 5 is avoided by a double security locking by means of the retaining system, 7 as well as the required tilting of the tube carrier 4.

In the following, the retaining system of the exemplary embodiments shown in the Figures and how it blocks pivoting the assistant's module 5 indirectly by blocking the tube carrier 4 in its working position W is described in more detail by reference to FIGS. 3 to 8.

In the shown embodiment, the retaining system 7 is arranged on the microscope body interface 3, as can be seen for example in FIG. 3, where the section of the microscope body interface 3, on which the retaining system 7 is mounted, is depicted. The other components of the pivotable optical assembly 1, shown in FIGS. 1 and 2, such as the tube carrier 4 and the assistant's module 5 are omitted in FIG. 3.

As can be seen in FIG. 3, the retaining element 12 of the retaining system 7, which is in its locking position L in FIG. 3, protrudes from the microscope body interface 3. In order to move the retaining element 7 from its locking position L into its release position R, the hand-operable control element 14 has to be actuated. In the shown embodiment, this can be done by turning the handle/knob 15 of the control element 14 about 180°. During this rotation, the control element 14 acts on the retaining element 7 moving it from its locking position L into its release position R, in which the retaining element 7 countersinks within the microscope body interface (see e.g. FIGS. 2 and 6).

FIG. 4 is a top view onto the pivotal optical assembly 1 of FIG. 1, namely the section thereof including the part of the microscope body interface 3, where the retaining system 7 is mounted. In contrast to FIG. 1, the knob 15 of the control element 14 is omitted in FIG. 4. In FIG. 4, one sees how the retaining element 12, in its locking position L, protrudes from the microscope body interface 3 and engages the tube carrier 4, this way blocking the tube carrier in its working position W. Contrary thereto, as shown in FIGS. 2A and 2B, the retaining element countersinks within the microscope body interface 3 when the retaining element of the retaining system 7 is in its release position R. In the release position R, the retaining element 12 disengages from the tube carrier 4 and allows tilting the tube carrier at its hinge 10 about the tilt axis 9.

In the following, the retaining system 7 of the shown embodiment and the functioning thereof is described in more detail with respect to FIGS. 4 to 8.

The retaining system 7 for a pivotable optical assembly 1 of the surgical microscope comprises a retaining element 12, a biasing member 13 and a control element 14. The retaining element is moveable from a locking position L into a release position R. The biasing member 13 forces the retaining element 12 into the locking position L. The hand-operable control element 14 acts on the retaining element 12 for moving it from the locking position L into the retaining position R.

In the embodiment shown in the figures, the retaining element 12 is a locking bolt 16. The locking bolt 16 is moveable linearly along a movement direction M between the locking position L and the release position R. The locking bolt 16 may comprise a locking tip 17, on the end protruding from the microscope body interface 3 in the locking position L. The locking tip 17 is beveled in the shown embodiment. In the locking position L the tip 17 engages with a locking recess 18 of the tube carrier 4, when the tube carrier 4 is in the working position W. That is, when the retaining element 12 is in the locking position L, its beveled locking tip 17 protrudes from the microscope body interface 3 and is placed in the locking recess 18 of the tube carrier 4, which opens against the movement direction M, in which the locking bolt 16 is moved from its release position R into the locking position L. When placed in the locking recess 18, the locking tip 17 provides a stop that blocks tilting of the tube carrier 4 perpendicular to the movement direction M, and thus indirectly blocks pivoting the assistant's module 5.

The biasing member 13 forces the retaining element 12 into the locking position L. In the shown embodiment, the biasing member 13 is designed as spring 19. The biasing member 13 may be a compressed spring 19, which engages with the biasing end 20 of the locking bolt 16, which is opposite the locking tip 17, and thus exerts a biasing force B pressing the retaining element 12 into the locking position L.

As can be seen, the locking tip 17 may protrude from the microscope body interface 3 in the locking position L (see FIG. 5), and may countersink within the microscope body interface 3 in the release position R (see FIG. 6). For leading the movement of the retaining element 12, in the shown embodiment, the locking bolt 16, between the locking position L and the release position R in its movement of direction M, a guidance 21 may be provided. In the shown embodiment, the microscope body interface 3 comprises the guidance 21. The guidance 21 may comprise a guide chamber 22, in which the locking bolt 16 is accommodated and mounted moveably between its locking position L and its release position R. Alternatively, or additionally, the guidance 21 may comprise a guide channel 23 accommodating a cam 24 of the retaining element 12.

In the shown embodiment, the locking bolt 16, representing the retaining element 12, comprises the cam 24 that engages with the control element 14. As will be explained in more detail below, the control element 14 acts on the cam 24 when moving the retaining element 12 from the locking position L into the release position R.

The cam 24 protrudes laterally from the locking bolt 16 in the shown embodiment. The locking bolt 16 comprises a transverse hole 33. Said transverse hole 33 may be threaded. The cam 24 may comprise a fastening section 25 that may be connected with the locking bolt 16. In the shown embodiment, the fastening section 25 comprises a thread 26 that is screwed into the transverse hole 33 of the locking bolt 16. The head 27 of the cam 24 is the part that protrudes laterally from the locking bolt 16, which is accommodated in the guide channel 23, and on which the control element 24 acts when moving the retaining element 12 from its locking position L against the biasing force B into the release position R.

For the guidance, the wall of the guide chamber 22 may comprise a slot extending in the direction of movement M that constitutes the guide channel 23. The head 27 of the cam 24 may be partly accommodated in the guide channel 23 and may partly project out of the guide chamber 22 and the guide channel 23. The outwardly projected head 27 is thus accessible for an interaction with the control element 24, which will now be described in more detail.

The control element 14 of the exemplary embodiment shown in the Figures, comprises the knob 15 already mentioned as well as a pusher 28 that selectively engages with the retaining element 12 for acting on it and moving it from the locking position L into the release position R. The pusher 28 may be pivotable or rotatable. In the shown embodiment, the pusher 28 is rotatable about a switching axis 29 in a switching direction S. In the shown embodiment, the switching axis 29 is perpendicular to the direction of movement M as well as to the tilting axis 9, and runs parallel to the pivot axis 11.

In the shown embodiment, the pusher 28 comprises an eccentric 30 that is mounted rotatable about the switching axis 29. The eccentric 30 comprises a disc-shaped body 31 and an axle 32 protruding from the disc-shaped body 31 offset from the center 41 of the disc 31. The handle 15 is imposed on the axle 32 such that rotating the handle 15 in the switching direction S rotates the axle 32 and thus the disc-shaped body 31 of the eccentric 30.

In the locking position L (see e.g. FIGS. 4 and 5), the pusher 28 is adjacent to, but spaced apart from the cam 24. Rotating the eccentric 30 brings the circumferential rim 34 of the disc 31 into contact with the head 27 of the cam 24 and pushes the cam 24 as well as the retaining element 12, to which it is fixed from the locking position L into the release position R. This movement of the retaining element 12 in the movement direction M is led by the guidance 21, in the shown embodiment, a guidance of the locking bolt 16 in the guide chamber 22 as well as the guidance of the cam 24 in the guide channel 23.

The control element 14 may take a closed position C, in which the control element 14 releases the retaining element 12 and the biasing member 13 forces the retaining element 12 into the locking position L. The closed position C is obtained when the marker 35 on the knob 15 is aligned with the closed position marker 36 on the microscope body interface 3 that is depicted by a closed lock.

When moving the control element 14 comprising a pusher 28 and the handle 15 (in the shown embodiment) about the switching axis 29 by 180°, the control element 14 obtains its open position O. In the open position O, the marker 35 of the knob 15 aligns with the open position marker 37 on the microscope body interface 3, depicted as an open lock, which position is shown for example in FIGS. 6 and 8.

For holding the control element 14 in the closed position C, in which the control element 14 releases the retaining element 12 and the biasing member 13 forces the retaining element 12 into the locking position L, and in the open position O, in which the control element 14 moves the retaining element 12 into the release position R, the retaining system 7 of the shown embodiment comprises a restraint 38. The restraint 38 holds the control element 14 in the closed position C and the open position O and a distinct actuation force is required before one may rotate the handle 15 in the switching direction S.

In the exemplary embodiment shown in the figures, the restraint 38 comprises a recess 39. In the shown embodiment, the recess 39 of the restraint 38 is designed as a notch 40 in the pusher 28. The notch 40 may be arranged at the circumferential rim 34 of the disc 31, opposite the axle 32 with respect to the center 41 of the disc 31.

In addition to the recess 39 arranged on the control element 14, the restraint 38 further comprises a detent 42, in the shown embodiment. The retaining system 7 may comprise a first detent 42 as well as a second detent 43.

In the shown exemplary embodiments of the figures, the retaining element 12 comprises a first detent 42 that engages with the recess 39, e.g. the notch 40 of the disc 31 in the open position O, shown for example in FIGS. 6 and 8. The open position O is thus achieved when the pusher 28 is switched in the switching direction S until the notch 40 in the circumferential rim 30 is aligned with the cam 24, the head 27 of which is then pressed, in the open position O, by the biasing force B into the notch 40.

The retaining system 7 of the shown embodiment further comprises a second detent 43 that engages with the recess 39 in the closed position C, which is shown for example in FIGS. 5 and 7. The second detent 43 is designed as a detent pin 44 that may be mounted in the microscope body interface 3 parallel with the locking bolt 16. In the shown embodiment, the detent pin 44 is designed as a ballpoint tensioning screw 45, the tip of which, which faces towards the pusher 28, comprises a spring mounted ball projecting towards the circumferential rim 34 of the pusher 28. In the closed position C, the recess 39, namely the notch 40 is aligned with the ballpoint of the ballpoint tensioning screw 45, which ballpoint is pushed, due to its tensioning, against the biasing force direction B into the notch 40 in the closed position C.

In the shown embodiment, the first detent 42 and the second detent 43 are arranged spaced apart from each other in relation to the movement direction M, along which the retaining element 12 is moved from its locking position L into its release position R. In the shown embodiment, the first detent 42 and the second detent 43 are arranged opposite to each other in relation to the switching axis 29 of the pusher 28. Thus, moving the control element 14 by 180° in the switching direction S is necessary in order to bring the control element 14 from its closed position C to its open position O, and vice versa.

The control element 14 further comprises a mounting frame 46. The mounting frame 46 is substantially disc-shaped with a hole in its center. On the outer side 47 of the mounting frame 46, the knob 15 is arranged. The disc 31 of the eccentric 30 is arranged on the opposite, inner side 48 of the mounting frame 46. The axle 32 extends through the hole in the mounting frame 46 into the handle 15, to which it is fastened rotationally fixed. So, rotating the handle 15 rotates the axle 32 of the eccentric 30. The mounting frame 46 is attached to the microscope body interface 3 by means of fastening screws 49, which are threaded into the inner side 48 of the mounting frame 46.

REFERENCE SIGNS

1 Pivotable optical assembly
2 Zero-degree assistant's module
3 Microscope body interface
4 Tube carrier
5 Assistant's module
6 Interface for assistant's tube
7 Retaining system
8 Interface for principal observer's tube
9 Tilt axis
10 Hinge
11 Pivot axis
12 Retaining element
13 Biasing member
14 Hand-operable control element
15 Handle/knob
16 Locking bolt
17 Locking tip
18 Locking recess
19 Spring
20 Biasing end
21 Guidance
22 Guide chamber
23 Guide channel
24 Cam
25 Fastening section
26 Thread
27 Head
28 Pusher
29 Switching axis
30 Eccentric
31 Disc-shaped body
32 Axle
33 Transverse hole
34 Circumferential rim
35 Marker on knob
36 Closed position marker
37 Open position marker
38 Restraint
39 Recess
40 Notch
41 Center of disc
42 First detent
43 Second detent
44 Detent pin
45 Ball point tensioning screw
46 Mounting frame
47 Outer side of mounting frame
48 Inner side of mounting frame
49 Fastening screw
50 spring-biased stud
51*l* fastening hole (left side)
51*r* fastening hole (right side)
W Working position
A Adjustment position
L Locking position
R Release position
M Movement direction
B Biasing force
S Switching direction
C Closed position
O Open position

The invention claimed is:

1. A pivotable optical assembly for a surgical microscope, the pivotable optical assembly comprising:
a microscope body interface for mounting the pivotable optical assembly on a microscope body;
a tube carrier including an interface for a principal observer's tube, the tube carrier being mounted on the microscope body interface by a hinge for rotation about a tilt axis relative to the microscope body interface between a working position and an adjustment position;
an assistant's module including an interface for an assistant's tube, the assistant's module being pivotable about a pivot axis relative to the microscope body when the tube carrier is in the adjustment position, and the assistant's module being blocked from pivoting about the pivot axis relative to the microscope body when the tube carrier is in the working position;
a retaining element moveable between a locking position in which the retaining element locks the tube carrier in the working position and a release position in which the retaining element releases the tube carrier to permit rotation of the tube carrier from the working position to the adjustment position, wherein the retaining element is arranged on the microscope body interface and is not captive on the tube carrier, and wherein the retaining element, in its locking position, protrudes from the microscope body interface and thereby engages the tube carrier and, in its release position, countersinks within the microscope body interface and thereby does not engage the tube carrier;
a biasing member forcing the retaining element into the locking position; and
a hand-operable control element acting on the retaining element for moving it from the locking position into the release position;
whereby pivoting of the assistant's module about the pivot axis is prevented when the retaining element is in the locking position and enabled when the retaining element is in the release position and the tube carrier is in the adjustment position.

2. The pivotable optical assembly according to claim 1, wherein the retaining element comprises a cam that engages with the control element.

3. The pivotable optical assembly according to claim 1, wherein the control element comprises a pusher that engages with the retaining element.

4. The pivotable optical assembly according to claim 1, further comprising a restraint to hold the control element in a closed position, in which the control element releases the retaining element and the biasing member forces the retaining element into the locking position, and in an open position, in which the control element moves the retaining element into the release position, wherein the restraint comprises a recess and at least one detent that engages with the recess, the recess being arranged on the control element.

5. The pivotable optical assembly according to claim 4, wherein the at least one detent comprises a first detent that engages with the recess in the open position.

6. The pivotable optical assembly according to claim 5, wherein the at least one detent further comprises a second detent that engages with the recess in the closed position.

* * * * *